(12) United States Patent
Hauser et al.

(10) Patent No.: US 11,141,274 B2
(45) Date of Patent: *Oct. 12, 2021

(54) METHOD OF TREATING A DEFECTIVE HEART VALVE

(71) Applicant: Edwards Lifesciences Corporation, Irvine, CA (US)

(72) Inventors: David L. Hauser, Newport Beach, CA (US); Jan Otto Solem, Bjarred (SE); David Alon, Zichron Yaacov (IL)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/028,719

(22) Filed: Sep. 22, 2020

(65) Prior Publication Data

US 2021/0015608 A1    Jan. 21, 2021

Related U.S. Application Data

(63) Continuation of application No. 16/803,455, filed on Feb. 27, 2020, now Pat. No. 10,799,361, which is a continuation of application No. 16/593,360, filed on Oct. 4, 2019, now Pat. No. 10,583,009, which is a continuation of application No. 15/443,289, filed on
(Continued)

(51) Int. Cl.
*A61F 2/24* (2006.01)

(52) U.S. Cl.
CPC ............ *A61F 2/246* (2013.01); *A61F 2/2418* (2013.01); *A61F 2/2436* (2013.01); *A61F 2/2445* (2013.01); *A61F 2/2466* (2013.01); *A61F 2/2412* (2013.01); *A61F 2210/0014* (2013.01);
(Continued)

(58) Field of Classification Search
CPC ...... A61F 2/2445; A61F 2/246; A61F 2/2442; A61F 2/2466; A61F 2/24; A61F 2220/0016
See application file for complete search history.

(56) References Cited

U.S. PATENT DOCUMENTS

| 3,671,979 A | 6/1972 | Moulopoulos |
| 3,689,942 A | 9/1972 | Rapp |

(Continued)

FOREIGN PATENT DOCUMENTS

| EP | 1472996 A1 | 11/2004 |
| FR | 2728457 A1 | 6/1996 |

(Continued)

*Primary Examiner* — Alexander J Orkin (57) ABSTRACT

A method of treating a defective heart valve includes inserting a delivery catheter through a small incision in a patient's groin, wherein the delivery catheter has a prosthetic device positioned along a distal end. The prosthetic device includes an insert member and an anchoring member. The insert member is positioned between the native heart valve and is allowed to self-expand. The anchoring member is preferably a stent connected to the insert member by at least one elongate member. The stent is deployed within an adjacent blood vessel for anchoring the insert member between the native leaflets. After deployment of the prosthetic device, the native leaflets of the heart valve form a tight seal against the insert member for preventing regurgitation through the native heart valve during ventricular systole.

18 Claims, 8 Drawing Sheets

Related U.S. Application Data

Feb. 27, 2017, now Pat. No. 10,441,423, which is a continuation of application No. 14/963,149, filed on Dec. 8, 2015, now Pat. No. 9,579,199, which is a continuation of application No. 14/636,011, filed on Mar. 2, 2015, now abandoned, which is a continuation of application No. 13/439,336, filed on Apr. 4, 2012, now Pat. No. 8,968,395, which is a continuation of application No. 11/756,530, filed on May 31, 2007, now abandoned.

(60) Provisional application No. 60/810,085, filed on Jun. 1, 2006.

(52) U.S. Cl.
CPC ............... *A61F 2220/0008* (2013.01); *A61F 2220/0016* (2013.01)

(56) References Cited

U.S. PATENT DOCUMENTS

| | | |
|---|---|---|
| 3,898,701 A | 8/1975 | La Russa |
| 4,306,319 A | 12/1981 | Kaster |
| 4,407,271 A | 10/1983 | Schiff |
| 5,167,239 A | 12/1992 | Cohen et al. |
| 5,332,402 A | 7/1994 | Teitelbaum |
| 5,397,351 A | 3/1995 | Pavcnik et al. |
| 5,554,184 A | 9/1996 | Machiraju |
| 5,607,465 A | 3/1997 | Camilli |
| 5,735,842 A | 4/1998 | Krueger et al. |
| 5,957,949 A | 9/1999 | Leonhardt et al. |
| 6,050,972 A | 4/2000 | Zadno-Azizi et al. |
| 6,210,432 B1 | 4/2001 | Solem et al. |
| 6,217,567 B1 | 4/2001 | Zadno-Azizi et al. |
| 6,287,334 B1 | 9/2001 | Moll et al. |
| 6,312,464 B1 | 11/2001 | Navia |
| 6,332,893 B1 | 12/2001 | Mortier et al. |
| 6,358,277 B1 | 3/2002 | Duran |
| 6,482,228 B1 | 11/2002 | Norred |
| 6,540,782 B1 | 4/2003 | Snyders |
| 6,602,288 B1 | 8/2003 | Cosgrove et al. |
| 6,605,112 B1 | 8/2003 | Moll et al. |
| 6,629,534 B1 | 10/2003 | St. Goar et al. |
| 6,709,456 B2 | 3/2004 | Langberg et al. |
| 6,730,121 B2 | 5/2004 | Ortiz et al. |
| 6,752,813 B2 | 6/2004 | Goldfarb et al. |
| 6,764,510 B2 | 7/2004 | Vidlund et al. |
| 6,767,362 B2 | 7/2004 | Schreck |
| 6,790,231 B2 | 9/2004 | Liddicoat et al. |
| 6,797,002 B2 | 9/2004 | Spence et al. |
| 6,808,483 B1 | 10/2004 | Ortiz et al. |
| 6,869,444 B2 | 3/2005 | Gabbay |
| 6,875,224 B2 | 4/2005 | Grimes |
| 6,994,092 B2 | 2/2006 | van der Burg et al. |
| 7,004,958 B2 | 2/2006 | Adams et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,070,616 B2 | 7/2006 | Majercak et al. |
| 7,077,862 B2 | 7/2006 | Vidlund et al. |
| 7,160,322 B2 | 1/2007 | Gabbay |
| 7,175,656 B2 | 2/2007 | Khairkhahan |
| 7,217,287 B2 | 5/2007 | Wilson et al. |
| 7,226,467 B2 | 6/2007 | Lucatero et al. |
| 7,252,682 B2 | 8/2007 | Seguin |
| 7,291,168 B2 | 11/2007 | Macoviak et al. |
| 7,320,665 B2 | 1/2008 | Vijay |
| 7,322,957 B2 | 1/2008 | Kletschka et al. |
| 7,381,220 B2 | 6/2008 | Macoviak et al. |
| 7,404,824 B1 | 7/2008 | Webler et al. |
| 7,559,936 B2 | 7/2009 | Levine |
| 7,678,145 B2 | 3/2010 | Vidlund et al. |
| 7,758,596 B2 | 7/2010 | Oz et al. |
| 7,785,366 B2 | 8/2010 | Maurer et al. |
| 7,815,580 B2 | 10/2010 | Viswanathan |
| 7,854,762 B2 | 12/2010 | Speziali et al. |
| 7,901,454 B2 | 3/2011 | Kapadia et al. |
| 7,927,370 B2 | 4/2011 | Webler et al. |
| 7,942,928 B2 | 5/2011 | Webler et al. |
| 8,007,428 B2 | 8/2011 | Vijay |
| 8,052,751 B2 | 11/2011 | Aklog et al. |
| 8,070,805 B2 | 12/2011 | Vidlund et al. |
| 8,092,525 B2 | 1/2012 | Eliasen et al. |
| 8,133,213 B2 | 3/2012 | Lashinski |
| 8,172,856 B2 | 5/2012 | Eigler et al. |
| 8,216,302 B2 | 7/2012 | Wilson et al. |
| 8,348,963 B2 | 1/2013 | Wilson |
| 8,449,606 B2 | 5/2013 | Eliasen et al. |
| 8,460,370 B2 | 6/2013 | Zakay |
| 8,486,136 B2 | 7/2013 | Maurer et al. |
| 8,579,967 B2 | 11/2013 | Webler et al. |
| 8,758,430 B2 | 6/2014 | Ferrari et al. |
| 8,758,432 B2 | 6/2014 | Solem |
| 8,778,017 B2 | 7/2014 | Eliasen et al. |
| 8,784,482 B2 | 7/2014 | Rahdert et al. |
| 8,845,717 B2 | 9/2014 | Khairkhahan et al. |
| 8,888,843 B2 | 11/2014 | Khairkhahan et al. |
| 8,888,844 B2 | 11/2014 | Eliasen et al. |
| 8,932,348 B2 | 1/2015 | Solem et al. |
| 8,968,395 B2 | 3/2015 | Hauser et al. |
| 9,161,837 B2 | 10/2015 | Kapadia |
| 9,232,998 B2 | 1/2016 | Wilson et al. |
| 9,232,999 B2 | 1/2016 | Maurer et al. |
| 9,259,317 B2 | 2/2016 | Wilson et al. |
| 9,289,297 B2 | 3/2016 | Wilson et al. |
| 9,474,605 B2 | 10/2016 | Rowe et al. |
| 9,579,199 B2 | 2/2017 | Hauser et al. |
| 9,636,223 B2 | 5/2017 | Khalil et al. |
| 10,583,009 B2 | 3/2020 | Hauser et al. |
| 10,799,361 B2 * | 10/2020 | Hauser ............... A61F 2/2436 |
| 2001/0021872 A1 | 9/2001 | Bailey et al. |
| 2002/0128708 A1 | 9/2002 | Northrup et al. |
| 2002/0198594 A1 | 12/2002 | Schreck |
| 2003/0050682 A1 | 3/2003 | Sharkey et al. |
| 2003/0050694 A1 | 3/2003 | Yang et al. |
| 2003/0078654 A1 | 4/2003 | Taylor et al. |
| 2003/0120341 A1 | 6/2003 | Shennib et al. |
| 2003/0187494 A1 | 10/2003 | Loaldi |
| 2004/0019378 A1 | 1/2004 | Hlavka et al. |
| 2004/0024414 A1 | 2/2004 | Downing |
| 2004/0092858 A1 | 5/2004 | Wilson et al. |
| 2004/0098081 A1 | 5/2004 | Landreville et al. |
| 2004/0117032 A1 | 6/2004 | Roth |
| 2004/0167539 A1 | 8/2004 | Kuehn et al. |
| 2004/0193259 A1 | 9/2004 | Gabbay |
| 2004/0225233 A1 | 11/2004 | Frankowski et al. |
| 2004/0243229 A1 | 12/2004 | Vidlund et al. |
| 2004/0267280 A1 | 12/2004 | Nishide et al. |
| 2005/0038508 A1 | 2/2005 | Gabbay |
| 2005/0038509 A1 | 2/2005 | Ashe |
| 2005/0055089 A1 | 3/2005 | Macoviak et al. |
| 2005/0070999 A1 | 3/2005 | Spence |
| 2005/0075719 A1 | 4/2005 | Bergheim |
| 2006/0058871 A1 | 3/2006 | Zakay et al. |
| 2006/0149360 A1* | 7/2006 | Schwammenthal .. A61F 2/2418 623/1.24 |
| 2006/0178700 A1* | 8/2006 | Quinn ................ A61F 2/2451 606/213 |
| 2006/0201519 A1 | 9/2006 | Frazier et al. |
| 2006/0241745 A1 | 10/2006 | Solem |
| 2007/0093890 A1 | 4/2007 | Eliasen et al. |
| 2007/0162071 A1 | 7/2007 | Burkett et al. |
| 2007/0198082 A1 | 8/2007 | Kapadia et al. |
| 2007/0219627 A1 | 9/2007 | Chu et al. |
| 2007/0255399 A1 | 11/2007 | Eliasen et al. |
| 2007/0265700 A1 | 11/2007 | Eliasen et al. |
| 2007/0270943 A1 | 11/2007 | Solem et al. |
| 2007/0282429 A1 | 12/2007 | Hauser et al. |
| 2008/0243245 A1 | 10/2008 | Thambar et al. |
| 2009/0048668 A1 | 2/2009 | Wilson et al. |
| 2009/0069885 A1 | 3/2009 | Rahdert et al. |
| 2009/0137968 A1 | 5/2009 | Rottenberg |
| 2010/0022948 A1 | 1/2010 | Wilson et al. |

(56) References Cited

U.S. PATENT DOCUMENTS

| | | |
|---|---|---|
| 2010/0023117 A1 | 1/2010 | Yoganathan et al. |
| 2010/0198347 A1 | 8/2010 | Zakay et al. |
| 2010/0298929 A1 | 11/2010 | Thornton et al. |
| 2011/0077733 A1 | 3/2011 | Solem |
| 2011/0184512 A1 | 7/2011 | Webler et al. |
| 2011/0224784 A1 | 9/2011 | Quinn |
| 2012/0143320 A1 | 6/2012 | Eliasen et al. |
| 2013/0338763 A1 | 12/2013 | Rowe et al. |
| 2014/0309732 A1 | 10/2014 | Solem |

FOREIGN PATENT DOCUMENTS

| | | |
|---|---|---|
| JP | S4211278 Y1 | 6/1967 |
| WO | 9930647 A1 | 6/1999 |
| WO | 0047139 A1 | 8/2000 |
| WO | 02062236 A1 | 8/2002 |
| WO | 03003949 A2 | 1/2003 |
| WO | 03028558 A2 | 4/2003 |
| WO | 03049619 A2 | 6/2003 |
| WO | 03003949 A3 | 1/2004 |
| WO | 2004012583 A2 | 2/2004 |
| WO | 2004014258 A1 | 2/2004 |
| WO | 2004021893 A1 | 3/2004 |
| WO | 2004030568 A2 | 4/2004 |
| WO | 2004045378 A2 | 6/2004 |
| WO | 2005007036 A1 | 1/2005 |
| WO | 2005027797 A1 | 3/2005 |
| WO | 2005069850 A2 | 8/2005 |
| WO | 2006032051 A2 | 3/2006 |
| WO | 2006049629 A1 | 5/2006 |
| WO | 2006111391 A1 | 10/2006 |
| WO | 2006127509 A2 | 11/2006 |
| WO | 2007050256 A2 | 5/2007 |

\* cited by examiner

METHOD OF TREATING A DEFECTIVE HEART VALVE

CROSS REFERENCE TO RELATED APPLICATION

This application is a continuation of U.S. patent application Ser. No. 16/803,455, filed Feb. 27, 2020, which is a continuation of U.S. patent application Ser. No. 16/593,360, filed Oct. 4, 2019, now U.S. Pat. No. 10,583,009, which is a continuation of U.S. patent application Ser. No. 15/443,289, filed Feb. 27, 2017, now U.S. Pat. No. 10,441,423, which is a continuation of U.S. patent application Ser. No. 14/963,149, filed Dec. 8, 2015, now U.S. Pat. No. 9,579,199, which is a continuation of U.S. patent application Ser. No. 14/636,011, filed Mar. 2, 2015, now abandoned, which is a continuation of U.S. patent application Ser. No. 13/439,336, filed Apr. 4, 2012, now U.S. Pat. No. 8,968,395, which is a continuation of U.S. patent application Ser. No. 11/756,530, filed May 31, 2007, now abandoned, which claims the benefit of U.S. Provisional Patent Application No. 60/810,085, filed Jun. 1, 2006, the entire disclosures of which are incorporated herein by reference in their entireties.

FIELD OF THE DISCLOSURE

The disclosure relates to the field of implantable cardiac prosthetics and in particular, to a cardiac prosthetic insert for reducing regurgitation through a heart valve, such as the aortic valve, and to methods of implanting the cardiac prosthetic insert.

BACKGROUND

Heart valve regurgitation, or leakage from the outflow to the inflow side of a heart valve, is a condition that occurs when a heart valve fails to close properly. Heart valve regurgitation decreases the efficiency of the heart, reduces blood circulation and adds stress to the heart. In early stages, heart valve regurgitation leaves a person fatigued and short of breath. If left unchecked, the problem can lead to congestive heart failure, arrythmias or death.

Regurgitation through the aortic valve, sometimes referred to as aortic insufficiency, is a serious problem that affects the health of millions of adults. The aortic valve is positioned on the left side of the heart between the left ventricle and the aorta. A healthy aortic valve opens to allow blood to flow from the left ventricle into the aorta during ventricular systole and then closes to prevent blood from flowing backward from the aorta into the left ventricle during ventricular diastole. However, over time, changes in the geometric configurations of the aortic annulus, or other causes such as calcification, infection and injury, may affect the functionality of the aortic valve. As a result, the aortic valve may not close completely during ventricular diastole, thereby leading to regurgitation.

Aortic insufficiency is typically treated by replacing the defective native valve with a prosthetic valve during open heart surgery. However, open-heart surgery is highly invasive and is therefore not an option for many high risk patients. Accordingly, in recent years, less invasive methods, such as percutaneous valve replacement, have been developed for replacing aortic valves. In an example, a prosthesis including a stent and a valve is crimped into a small profile and then delivered into the heart via a percutaneous route. Once located at the treatment site, the prosthesis is expanded to replace the function of the native aortic valve. Although percutaneous valve replacement has shown great promise, there are still challenges with respect to delivery techniques, perivalvular leakage and durability of the valve. Furthermore, when possible, it may be desirable to repair, rather than replace, the native valve.

SUMMARY

Accordingly, disclosed herein is a device and method of use for treating heart valve disease, involving in exemplary embodiments, a minimally invasive procedure that does not require extracorporeal circulation. Certain embodiments of such a device and method desirably are capable of reducing or eliminating regurgitation through a heart valve. It is also desirable that embodiments of such a device and method be well-suited for delivery in a percutaneous or minimally-invasive procedure. It is also desirable that embodiments of such a device and method be well-suited for repairing an aortic valve. It is also desirable that such a device be safe, reliable and easy to deliver. It is also desirable that embodiments of such a device and method be applicable for improving heart valve function for a wide variety of heart valve defects. It is also desirable that embodiments of such a device and method be capable of improving valve function without replacing the native valve.

Various embodiments of the present disclosure provide improved devices and methods for improving the function of a defective heart valve. Particular embodiments can be configured to be implanted in a heart using a percutaneous or minimally invasive procedure wherein extracorporeal circulation is not required.

In one representative embodiment of the present disclosure, a prosthetic device includes an anchoring member and an insert member configured for deployment between the leaflets of a native valve, such as the aortic valve. The insert member is desirably shaped to fill the gap(s) between the leaflets for creating a tight seal during ventricular diastole and thereby minimizing or preventing regurgitation through the aortic valve. The insert member is desirably sized such that the native leaflets engage the surfaces of the insert member. When configured for use with a typical aortic valve, the insert member desirably includes three arms extending radially outward from a central region. Each of the arms is shaped for placement between adjacent leaflets of the aortic valve. The anchoring member is provided for securing the insert member in its deployed position. In exemplary embodiments, the anchoring member takes the form of a stent configured for deployment in the ascending aorta. In one variation, the insert member can be configured (e.g., with two arms) for use with an aortic valve having only two leaflets. In another variation, the insert member can be configured for use in a pulmonary valve for treating pulmonary insufficiency.

In another representative embodiment of the present disclosure, a prosthetic device includes an anchoring member formed of a stent and an insert member configured for deployment between the leaflets of a native aortic valve. The anchoring member desirably includes a valve member for providing unidirectional flow. The anchoring member is desirably configured for delivery into an ascending aorta. The stent is expanded, either by self-expansion or by balloon expansion, such that the stent is anchored in the aorta. After deployment, the valve member in the stent prevents or minimizes blood from flowing backward through the aorta. The insert member is delivered into the native aortic valve to improve the native valve function. Accordingly, two separate valves (e.g., stented valve and native valve) work in tandem for preventing regurgitation through the aortic annulus. By deploying the insert member in the native valve, the native valve is allowed to function as it should and blood enters the coronary arteries in a substantially natural manner. The stented valve supplements the function of the native valve. If desired, the stented valve could be constructed to close before or after (desirably after) the native valve to further influence and improve the native valve function and also to improve hemodynamics.

In a representative embodiment, a system and method are provided for treating a defective heart valve. The system includes a prosthetic device including an anchoring member and an insert member. The system further includes a delivery catheter for delivering the prosthetic device into the heart via a percutaneous approach. The delivery catheter desirably includes an elongate sheath having a lumen sized to receive the prosthetic device. In exemplary embodiments, the prosthetic device is held within the sheath in a collapsed configuration during advancement through the subject's vasculature. In one variation, the sheath is configured for retrograde advancement and may be configured with a deflectable end portion for facilitating navigation around the aortic arch. After reaching the treatment site, the sheath is moved proximally relative to the prosthetic device to eject the device from the sheath. The device is then allowed to expand such that the insert conforms to the gaps in the aortic valve and the anchoring member engages the inner wall of the aorta.

In another representative embodiment of the present disclosure, a prosthetic device includes an anchoring member and an insert member having three expandable arms configured for deployment between the gaps in an insufficient aortic valve. Each arm desirably includes an expandable region that opens in a manner somewhat similar to a parachute for preventing regurgitation. During ventricular systole, each expandable region collapses such that the flow of blood through the aortic valve is not impeded.

In a certain representative embodiment of the present disclosure, a prosthetic device includes an insert member configured for deployment within an aortic valve and an anchoring member configured for securement within the left ventricle. An elongate body portion is provided for coupling the insert member to the anchoring member. If one variation, the prosthetic device can be delivered in multiple stages. In a first stage, the anchoring member is delivered and is then allowed to grow into the heart wall. After sufficient in-growth has occurred, in a second stage, the insert member is attached to the anchoring member.

In another representative embodiment of the present disclosure, a prosthetic device includes an anchoring member and an insert member configured for deployment between anterior and posterior leaflets of a mitral valve. The insert member is desirably shaped to fill the gap between native leaflets for preventing regurgitation through the mitral valve. The insert member is sized such that the mitral valve leaflets engage the surfaces of the insert member to create a tight seal during ventricular systole. In a variation of this embodiment, one or more passageways are provided through the insert member for allowing blood to flow through the device in one direction to further improve valve function.

The foregoing and other features will become more apparent from the following detailed description of several embodiments, which proceeds with reference to the accompanying figures.

DETAILED DESCRIPTION OF SEVERAL EMBODIMENTS

I. Explanation of Terms

Unless otherwise noted, all technical and scientific terms used herein have the same meaning as commonly understood by one of ordinary skill in the art to which this disclosure belongs. In order to facilitate review of the various embodiments of the disclosure, the following explanation of terms is provided:

The singular terms "a", "an", and "the" include plural referents unless context clearly indicates otherwise. The term "or" refers to a single element of stated alternative elements or a combination of two or more elements, unless context clearly indicates otherwise.

The term "includes" means "comprises." For example, a device that includes or comprises A and B contains A and B, but may optionally contain C or other components other than A and B. Moreover, a device that includes or comprises A or B may contain A or B or A and B, and optionally one or more other components, such as C.

The term "proximal" refers to a portion of an instrument closer to an operator, while "distal" refers to a portion of the instrument farther away from the operator.

The term "subject" refers to both human and other animal subjects. In certain embodiments, the subject is a human or other mammal, such as a primate, cat, dog, cow, horse, rodent, sheep, goat, or pig. In a particular example, the subject is a human patient.

Although methods and materials similar or equivalent to those described herein can be used in the practice or testing of the present disclosure, suitable methods and materials are described below. In case of conflict, the present specification, including terms, will control. In addition, the materials, methods, and examples are illustrative only and not intended to be limiting.

II. An Anatomical Overview of the Human Heart

Figure 1:
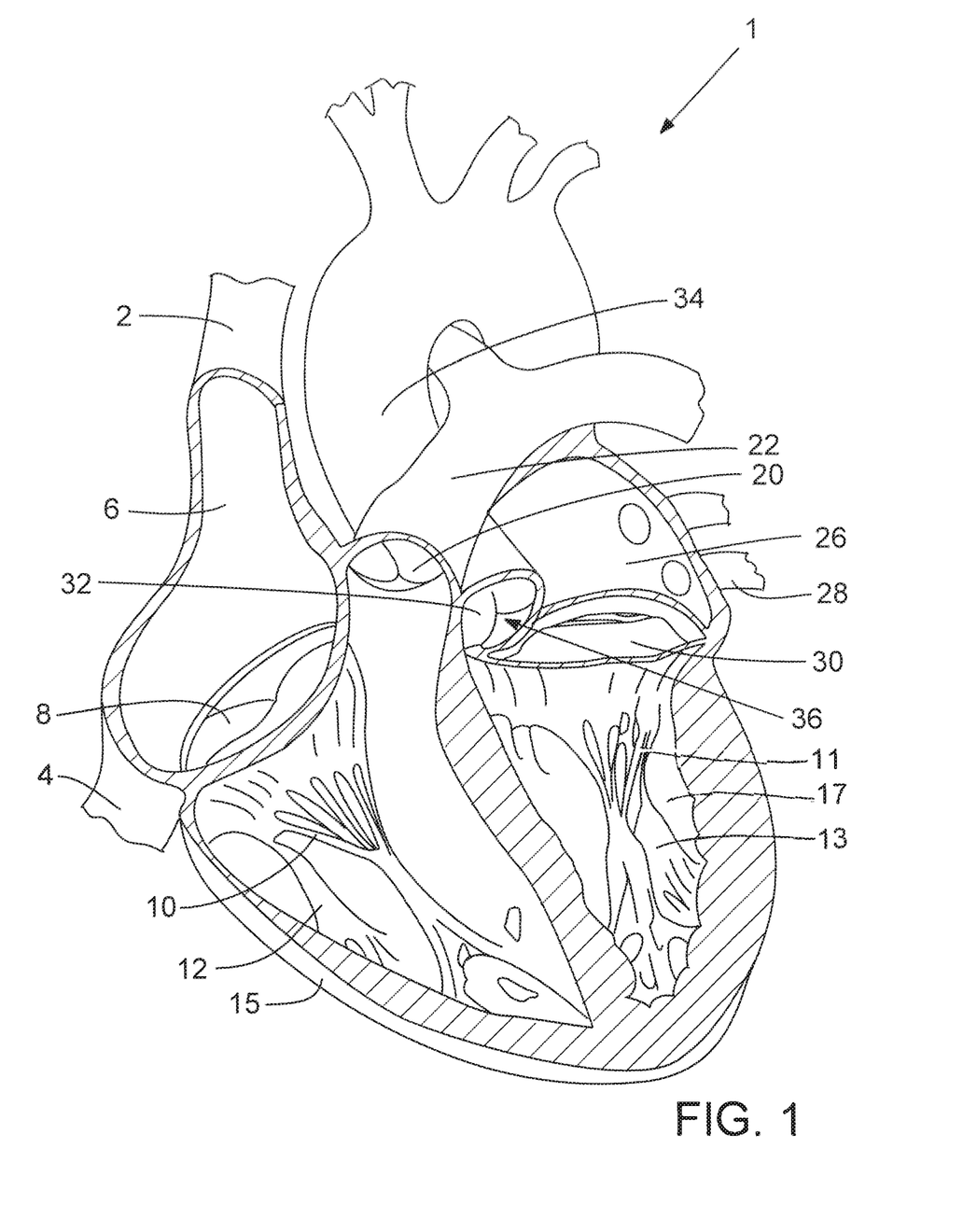
FIG. 1 illustrates a cross-sectional view of a heart.

With reference to FIG. 1, a cross-sectional view of a heart 1 is provided. Blood flows through the superior vena cava 2 and the inferior vena cava 4 into the right atrium 6 of the heart 1. The tricuspid valve 8 controls blood flow between the right atrium 6 and the right ventricle 15. The tricuspid valve 8 is closed when blood is pumped out from the right ventricle 15 to the lungs. Thereafter, the tricuspid valve 8 is opened to refill the right ventricle 15 with blood from the right atrium 6. Free edges of leaflets of the tricuspid valve 8 are connected via the chordae tendinae 10 to the papillary muscles 12 in the right ventricle 15 for controlling the movements of the tricuspid valve 8. Blood from the right ventricle 15 is pumped through the pulmonary valve 20 to the pulmonary artery 22, which branches into arteries leading to the lungs.

After exiting the lungs, the oxygenated blood flows through the pulmonary veins 28 and enters the left atrium 26 of the heart 1. The mitral valve 30 controls blood flow between the left atrium 26 and the left ventricle 17. The mitral valve 30 is closed during ventricular systole when blood is ejected from the left ventricle 17 into the aorta 34. Thereafter, the mitral valve 30 is opened to refill the left ventricle 17 with blood from the left atrium 26. Free edges of leaflets of the mitral valve 30 are connected via the chordae tendinae 11 to the papillary muscles 13 in the left ventricle for controlling the movements of the mitral valve 30. Blood from the left ventricle 17 is pumped through the aortic valve 32 into the aorta 34 which branches into arteries leading to all parts of the body. The aortic valve 32 includes three leaflets (also known as flaps or cusps) collectively denoted by reference numeral 36. Leaflets 36 open and close to control the flow of blood into the aorta 34 from the left ventricle 17 of the heart as it beats.

III. Prosthetic Device for Reducing Regurgitation Through a Heart Valve

The efficiency of the heart may be seriously impaired if any of the heart valves is not functioning properly. For example, heart valves may lose their ability to close properly due to dilation of an annulus around the valve or a flaccid, prolapsed leaflet. The leaflets may also have shrunk due to disease, such as rheumatic disease, thereby leaving a gap in the valve between the leaflets. The inability of the heart valve to close will cause blood to leak backwards (opposite to the normal flow of blood), commonly referred to as regurgitation, through the aortic valve into the left ventricle. Regurgitation may seriously impair the function of the heart since more blood will have to be pumped through the regurgitating valve to maintain adequate circulation.

Embodiments of the present disclosure provide devices and methods for improving the function of a defective heart valve, such as an aortic valve. The devices and methods disclosed herein are desirably delivered into a subject's heart using percutaneous or minimally invasive surgical methods. Accordingly, desirable delivery methods described herein do not require extracorporeal circulation (e.g., blood from a subject's circulation being routed outside the body to have a process applied to and then, returned of the subject's circulation). For example, in one embodiment, a delivery catheter (or similar delivery device) is inserted through an incision in the chest wall and then through the cardiac tissue (e.g., through the apex of the heart) into a chamber of the patient's beating heart. The delivery catheter can allow a prosthetic device to be delivered into the heart in a collapsed configuration and then expanded within the heart for treating a defective heart valve. Because the desired delivery methods do not require extracorporeal circulation, complications are greatly reduced as compared with traditional open-heart surgery.

Figure 2:
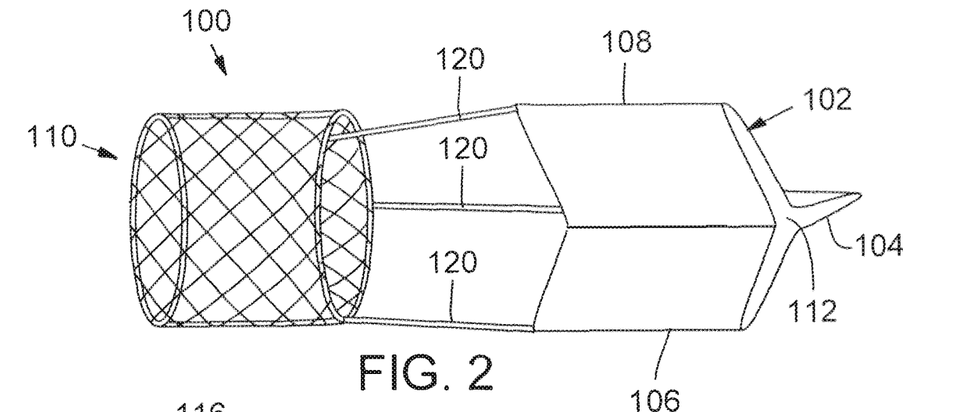
FIG. 2 is a perspective view of a prosthetic device including an anchoring member and an insert member configured for deployment between leaflets of a native aortic valve.

FIG. 2 illustrates an example of a prosthetic device 100 which can be employed to reduce or eliminate regurgitation through a heart valve, such as the aortic valve. The prosthetic device 100 includes an insert member 102 and an anchoring member 110. The insert member 102 desirably includes a solid outer surface for contacting native valve leaflets, such as the native aortic valve leaflets. As used herein, a "solid" surface refers to a non-perforated surface that does not include any openings through which blood can pass. As illustrated in FIG. 2, the insert member 102 includes a first extension portion, or arm, 104, a second extension portion, or arm, 106 and a third extension portion, or arm, 108. The extension portions 104, 106, 108 desirably are equally angularly-spaced about a central portion 112 of the insert member 102 and extend radially outwardly therefrom. The prosthetic device 100 can include a plurality of spacers or connecting members 120 for mounting the insert member 102 at a position spaced from the anchoring member 110. As shown in FIG. 2, three such spacers or connecting members 120 are provided in the illustrated embodiment for coupling the insert member 102 to the anchoring member 110.

In the illustrated embodiment, the anchoring member 110 takes the form of a self-expanding or balloon-expandable stent having an open-frame construction as depicted in FIG. 2. The anchoring member can be made of various suitable expandable and/or elastic materials, such as stainless steel, titanium, shape memory alloys, or other biocompatible metals. In one example, the anchoring member 110 is self-expanding and formed of shape memory alloys, such as nickel titanium (NiTi) shape memory alloys, as marketed, for example, under the trade name Nitinol. In another example, the anchoring member 110 is balloon-expandable and formed of stainless steel or other suitable materials.

In particular embodiments, the anchoring member 110 comprises a stent having a plurality of angularly-spaced axial struts, or support members, that extend axially (longitudinally) of the member. The anchoring member 110 can also include a plurality of axially-spaced, circumferential bands, or struts, attached to the axial struts. The circumferential struts are formed with multiple bends that allow the anchoring member 110 to be compressed to a smaller diameter for delivery to an implantation site and expanded to its functional size for anchoring the insert member 102 to the heart. The circumferential struts can include a plurality of linear strut members arranged in a zig-zag or saw-tooth configuration defining bends between adjacent strut members. In other examples, one or more of the circumferential bands can have a curved or serpentine shape rather than a zig-zag shape. In variations, the anchoring member 110 may further include fixation or attachment members, such as barbs, staples, flanges, hooks, and the like along the exterior of the anchoring member 110 for enhancing the ability of the anchoring member 110 to anchor insert member within the aorta. Further details of exemplary stents that can be employed in the embodiments disclosed herein are disclosed in U.S. Pat. Nos. 6,730,118, 6,767,362, and 6,908,481, each of which is incorporated herein by reference in its entirety.

Although the anchoring member is primarily described in the form of a stent, it will be appreciated that a wide variety of anchoring mechanisms may be used while remaining within the scope of the present disclosure. For example, the anchoring member can be formed by one or more retainers. In a particular example, the anchoring member can be a plurality of spaced-apart retainers that extend outwardly to contact tissue near or within the heart valve annulus. The retainers are sized and configured to secure the body to the heart valve annulus. For instance, the one or more retainers can be circular bands formed of polyethylene, polypropylene, polycarbonate, nylon, polytetrafluoroethylene, polyurethane, stainless steel, Nitinol, titanium, polyimide, polyester, shape-memory material, or a mixture thereof. The one or more retainers can include protrusions, barbs, needles, hooks, and like engagement members for assisting with anchoring the prosthetic device within the heart valve.

Figures 3, 4, 5:
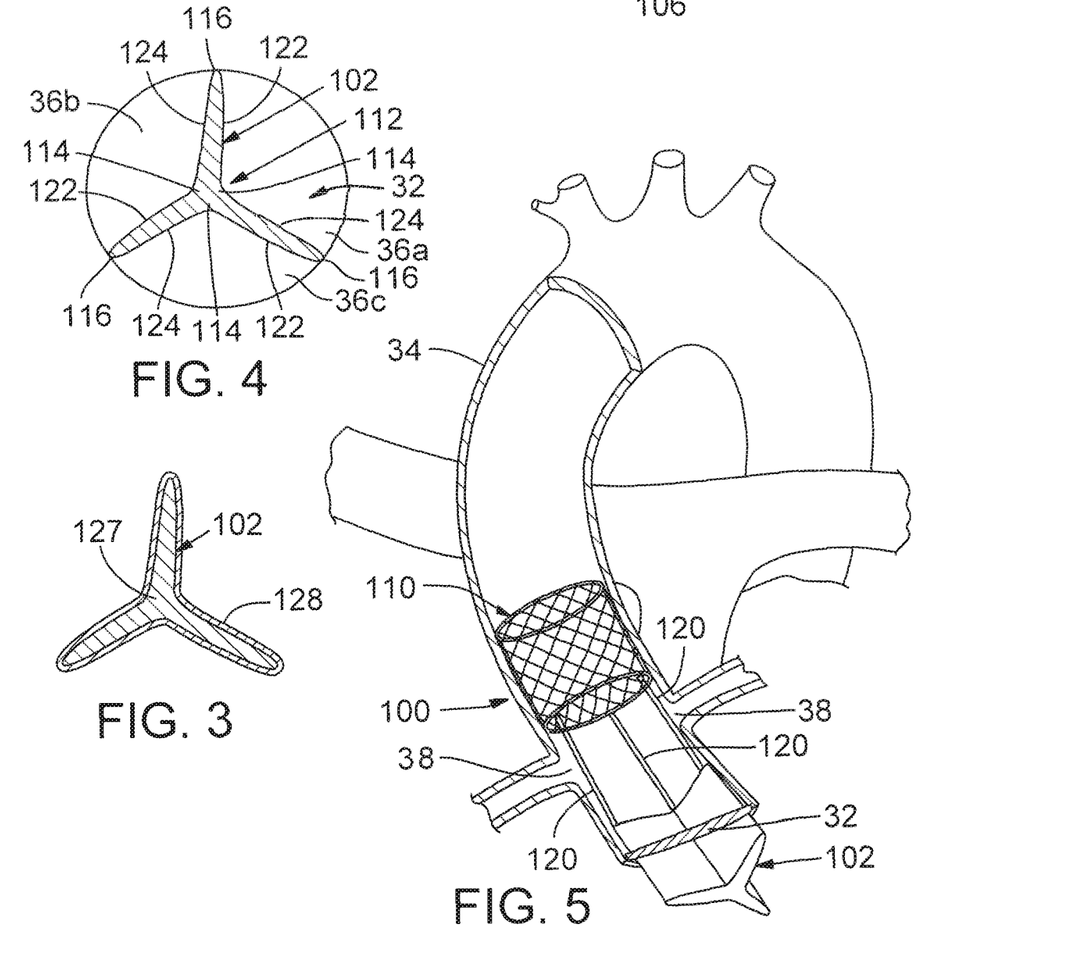
FIG. 3 is a cross-sectional view of an insert member with an outer coating of biocompatible material.
FIG. 4 is a cross-sectional view of the insert member of FIG. 2 positioned in an aortic valve.
FIG. 5 is a partial cut-away view of the aorta illustrating the prosthetic device of FIG. 2 deployed within a subject to treat aortic insufficiency.

The insert member 102 is configured for insertion between the leaflets of an insufficient aortic valve so as to fill the gap between the leaflets. In one specific example, the insert member 102 exhibits sufficient rigidity to substantially maintain its deployed shape and is resilient and/or flexible enough to be compressed to a reduced diameter for delivery in a delivery sheath. The insert member can be formed from plastic, metal (e.g., shape memory metal) or other biocompatible material suitable for implantation into a subject. In particular examples, as illustrated in FIG. 3, the insert member 102 can include an inner support layer 127 and an outer layer or sheath 128. The outer layer 128 can be formed of a biocompatible material, such as a cloth-like or fabric material (natural or synthetic) or a biological material, such as collagen or biological tissue material in order to protect the native leaflets from damage (e.g., to inhibit abrasion that could occur in response to engagement and disengagement of the leaflets). For instance, smooth animal pericardium such as equine, bovine, porcine or other animal pericardial tissue which is compatible with the native leaflets may be included within the outer layer 128. Such tissue may be tanned or fixed by a suitable tanning environment or the pericardium can be cross-linked with glutaraldehyde and heparin bonded by a detoxification process. In a certain example, the biological tissue material can be one of the NO-REACT® natural tissue products exhibit improved biocompatibility and mitigate calcification and thrombus formation. The outer layer 128 can cover the entire outer surface of the inner layer 127 or selected portions of the outer surface, such as those portions that come into contact with the native leaflets.

In certain examples, the diameter of the insert member 102 is similar to the diameter of the native aortic valve such that each of the extension portions extends into a cusp between leaflets in the aortic valve. As a result, the insert member 102 of the device 100 remains centered within the aortic valve after deployment. In certain examples, the diameter of the insert member is about 18 mm to about 26 mm, with about 22 mm being a specific example. The diameter of the insert member 102 can be slightly smaller as compared to the diameter of the anchoring member 110. This configuration allows the insert member to collapse or fold-down to a reduced diameter for delivery in a delivery sheath. Additionally, the length of the insert member can vary. For example, in one embodiment, the length of the insert member is approximately the same size as the length of the anchoring member. In other examples, the length of the insert member is greater or smaller than that of the anchoring member. In certain examples, the length of the insert member is about 20 mm to about 30 mm, with about 25 mm being a specific example.

As illustrated in FIG. 4, the cross-sectional profile of the insert member 102 can be shaped such that the native leaflets 36a, 36b, 36c are capable of contacting the sides of the insert member 102 to create a tight seal during ventricular diastole. For example, the three spaced apart extensions or arms 104, 106 and 108 extend radially outward from a central region 112 of the insert member 102. In certain examples, the arms taper in width from the central portion to the outer ends of the extension portions. For example, each arm includes a first end 114 and a second end 116. The first end 114 is of a greater width than the second end 116. The arms each include a first side 122 and a second side 124, each of which side is configured for contact with a native leaflet. The ends 114, 116 and the sides 122, 124 can be configured with smooth edges to minimize or eliminate hemolytic effects. Further, each of the arms is configured to fill a gap between adjacent leaflets of an aortic valve, thereby preventing regurgitation through the aortic valve. The contact surfaces of the arms can exhibit sufficient compliancy and/or flexibility to allow the native leaflets to engage the insert member 102 and create a tight seal without damaging the leaflets. For example, as described above, each arm can include biocompatible material, such as collagen or pericardial tissue to inhibit abrasion that could occur in response to engagement or coaptation of the arms with the native leaflets.

When used to treat an aortic valve, the cross-sectional profile of the insert member can be minimized to limit resistance to blood flow from the left ventricle into the aorta when the aortic valve is fully open. Furthermore, one or both ends of the insert member may be tapered or rounded such that there are no flat surfaces facing perpendicular to the flow of blood. With respect to the illustrated embodiment, it will be appreciated that the prosthetic device is capable of minimizing or preventing regurgitation without utilizing any moving parts. The device can therefore achieve greater durability as compared with alternative heart valve repair and replacement techniques that utilize moving parts.

The insert member 102 can be configured with expandable structures, such as moveable flaps, to further impede regurgitation through the aortic valve. Each expandable structure can be configured to fill a gap between adjacent native valve leaflets. In one example, the movable flaps can be configured to open in a manner similar to that of a parachute to block regurgitation of blood between the leaflets of the native aortic valve. During ventricular systole, the moveable flaps collapse to allow blood to flow from the left ventricle, through the native aortic valve and into the aorta in a substantially unimpeded manner. Additional details regarding an expandable insert member (e.g., valve portion) can be found in Applicant's co-pending U.S. application Ser.

No. 11/407,582 (U.S. Patent Publication No. 2006/0241745), filed on Apr. 19, 2006, which is hereby incorporated by reference in its entirety. Principles and features of the expandable prosthetic devices described in the '582 Application, which are configured for use with a mitral valve, are also applicable to the devices described herein for use in the aortic valve.

As mentioned above and as illustrated in FIG. 2, the prosthetic device 100 includes a plurality of spacers or connecting members 120. Each connecting member can be generally cylindrical in shape, although any other suitable shape may be employed. In certain examples, the length of each connecting member is about 6 mm to about 14 mm, with about 10 mm being a specific example. Each connecting member preferably couples an arm of the insert member 102 to the anchoring member 110. The connecting members 120 can assist in stabilizing the insert member 102. Each connecting member desirably exhibits sufficient rigidity to substantially maintain the insert member in a fixed position relative to the anchoring member. The connecting members can be formed of plastic, metal or other biocompatible material suitable for implantation into a subject. The connecting members 120 also minimize interference of the prosthetic device with blood flow to the coronary arteries by allowing the anchoring member 110 to be positioned above the coronary ostia and the insert member 102 positioned in the native aortic valve.

As best illustrated in FIG. 4, the native leaflets 36a, 36b, 36c of the aortic valve 32 contact the insert member 102 during ventricular diastole to create a tight seal. By allowing the aortic valve 32 to create a tight seal, regurgitation from the aorta into the left ventricle is minimized or prevented. During ventricular systole, the native leaflets open as they do naturally to allow blood to be pumped from the left ventricle into the aorta. As can be seen in FIG. 4, the cross-sectional area of the insert member 102 is relatively small as compared with the flow area through the aortic annulus. Accordingly, in the illustrated embodiment, the insert member 102 will not substantially impede the flow of blood through the aortic valve during ventricular systole.

With reference to FIG. 5, the prosthetic device 100 is illustrated after deployment within a subject. As illustrated in FIG. 5, the anchoring member 110 is deployed in the aorta above the aortic valve, such as above the ostia of the coronary arteries 38 such as to not interfere with the flow of blood through the coronary arteries. The insert member 102 is deployed within the native aortic valve to improve the function of the aortic valve. For example, the insert member 102 is positioned within the native aortic valve with each arm 104, 106 and 108 extending between adjacent edges of two leaflets such that the leaflets of the aortic valve 32 coapt with the arms 104, 106 and 108. The connecting members 120 extend from the anchoring member 110 to the insert member 102 for maintaining the insert member 102 in a substantially fixed position. During ventricular diastole, the leaflets of the aortic valve 32 close and press against the walls of the insert member to create a tight seal. Although the native leaflets in an insufficient or defective aortic valve may not be able to close completely, the arms of the insert member 102 fill the gaps such that little or no blood is allowed to pass from the aorta back into the left ventricle.

As shown, the native aortic valve is not excised and continues to function in a substantially normal manner. As a result, over time, it may be possible to remove the prosthetic device if the native valve is able to heal itself or if an alternative treatment is found.

Figure 6:
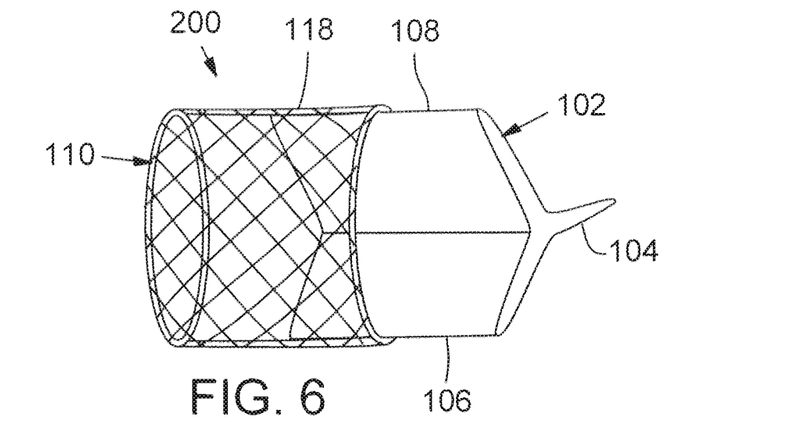
FIG. 6 is a perspective view illustrating an embodiment of a prosthetic device wherein the insert member is directly attached to the anchoring member.

With reference to FIG. 6, a prosthetic device 200 according to another embodiment is shown. Prosthetic device 200 includes an insert member 102 and an anchoring member 110. The insert member 102 in the illustrated embodiment is directly coupled to the anchoring member 110 rather than via the connecting members 120. For example, the insert member can be coupled to the anchoring member 110 via the proximal end 118 of the insert member 102, for example with the proximal end of the insert member 102 received partially within and surrounded by an end portion of the anchoring member 110. The diameter of the insert member 102 in the illustrated embodiment is less than the diameter of the anchoring member 110. This configuration allows the insert member 102 to be collapsed or folded during implantation, and then deployed within the valve.

Figure 7:
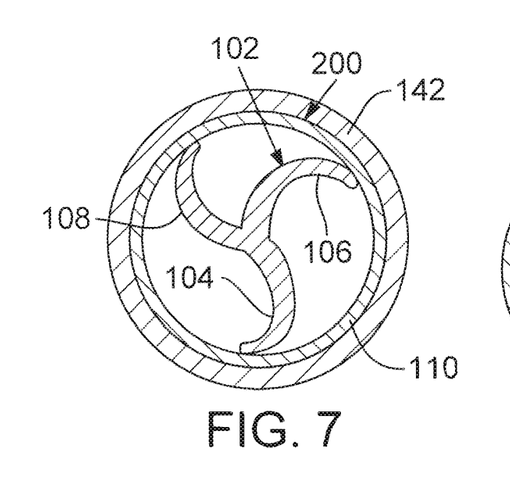
FIG. 7 is a cross-sectional view of the insert member of FIG. 6 contained within a sheath in a contracted condition for delivery to a treatment site.
Figure 8:
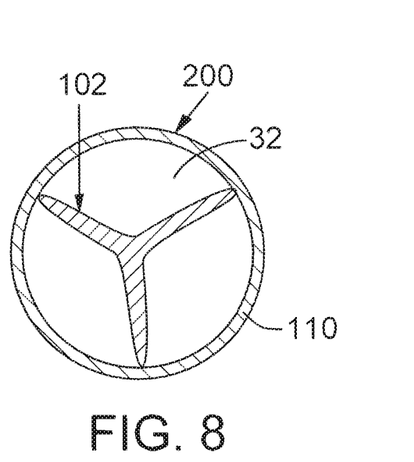
FIG. 8 illustrates the insert member of FIG. 6 after being ejected from the sheath and expanding into an expanded condition.

The disclosed prosthetic devices can be configured to be delivered in a percutaneous or minimally invasive procedure in which only a small access incision is required. In one example, the prosthetic device can be configured so that it can be crimped or otherwise collapsed into a smaller profile and then placed in a delivery sheath for advancement to the treatment site. FIG. 7, for example, illustrates a prosthetic device 200 in a collapsed condition within a sheath 142. As shown, the insert member 102 can be configured to be sufficiently flexible such that the arms can be folded or caused to assume a curved profile to temporarily reduce the profile of the insert during delivery. After being ejected from the sheath 142, the anchoring member 110 and insert member 102 expand to a fully expanded condition as shown in FIG. 8. When delivered to the aortic valve in a percutaneous procedure, it may be desirable to utilize a deflectable sheath to facilitate navigation through the patient's vasculature and around the aortic arch. Details regarding various embodiments of a deflectable sheath configured to deliver a therapy device to an aortic valve can be found in Applicant's co-pending U.S. application Ser. No. 11/152,288, filed Jun. 13, 2005, entitled "Heart Valve Delivery System," which is hereby incorporated by reference in its entirety.

Figure 9A:
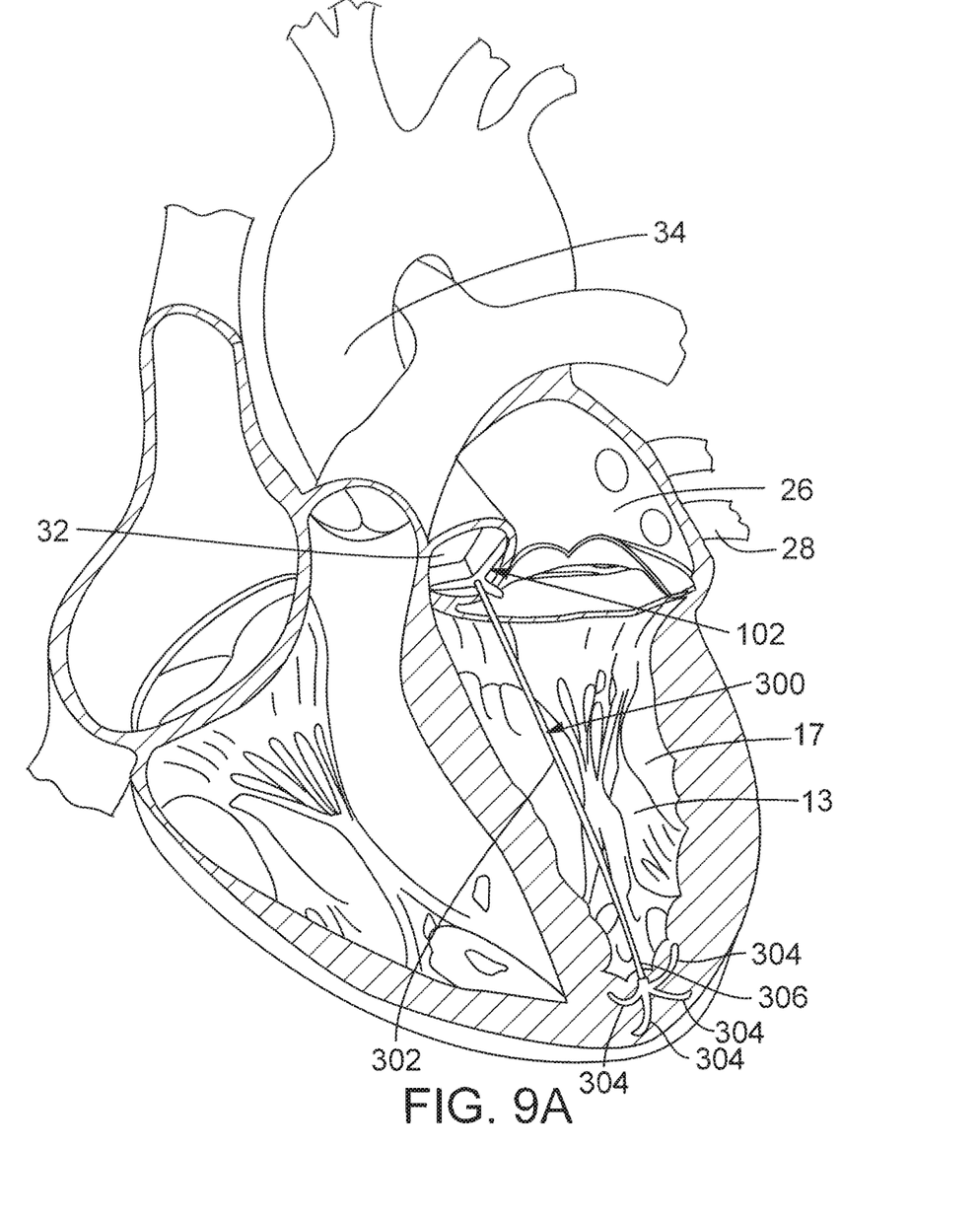
FIG. 9A is a perspective view of a prosthetic device including an insert member for deployment in the aortic valve and an anchoring member with engagement members for securement to the left ventricle.

FIG. 9A illustrates a prosthetic device 300 that can be used to reduce or eliminate heart valve regurgitation, such as aortic valve regurgitation. In this embodiment, the prosthetic device includes an insert member 102 configured for insertion into the aortic valve and an anchoring member 302 configured for securement to the muscular wall in the left ventricle. The anchoring member 302 can include a plurality of engagement members 304, such as hooks or fingers, that penetrate tissue along the muscular wall for securing the insert member 102 to the heart. The engagement members 304 can be formed of any biocompatible material, such as biocompatible metals or plastics, which is capable of penetrating the left ventricle muscular wall to secure the insert member 102 to the heart without substantially impairing the wall. The anchoring member 302 can include an elongate body portion, or shaft, 306 which couples the engagement members 304 to the insert member 102. In one example, the elongate body portion 306 and the engagement members 304 can be formed from a single piece of material. In another example, the elongate body portion 306 and the engagement members 304 can be separately formed and subsequently coupled to one another by any suitable means, such as welding. The elongate body portion 306 and the engagement members 304 can be formed of the same or different materials depending on the material properties (elasticity, rigidity, resilience and the like) desired for each part of the device 300.

The prosthetic device 300 can be positioned within the heart to minimize aortic valve regurgitation by positioning the plurality of engagement members 304 in the left ventricle near the left ventricular apex. In the illustrated embodiment, a plurality of fingers or hooks penetrates tissue along the left ventricle muscular wall near the left ventricular apex. The insert member 102 is positioned in the aortic valve annulus such that an upper portion and lower portion extend above and below the native aortic valve and the arms of the insert member 102 are aligned with coaptions of the three cusps of aortic valve so each leaflet moves up and down between the insert arms.

Figure 9B:
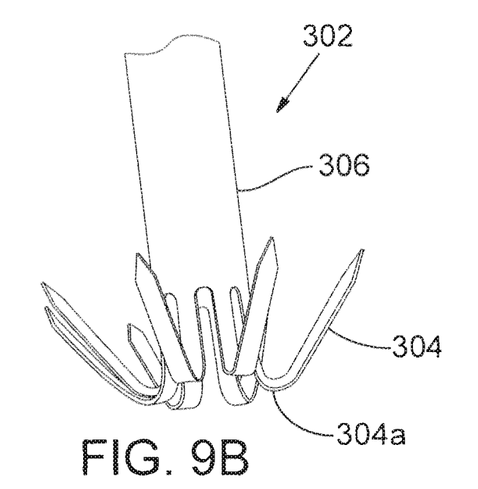
FIG. 9B is an exploded view of an exemplary embodiment of a plurality of engagement members shown in an expanded state.
Figure 9C:
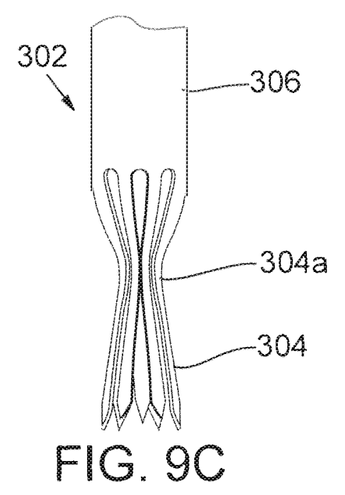
FIG. 9C is a perspective view of the plurality of engagement members of FIG. 9B shown in a compressed state for delivery to the heart.

FIGS. 9B and 9C illustrate the lower end portion of an anchor member 302 with a plurality of engagement members 304 in the form of elongated prongs. The elongated prongs 304 are desirably configured to self-expand from the compressed configuration of FIG. 9C to a "flowered" or expanded configuration of FIG. 9B when advanced out of a delivery sheath. This flowering is desirably achieved with a self curving area 304a that deflects the prongs 304 radially outward from the center of the body 502 and rearward toward the second end of the body. The prongs 304 are desirably pointed or barbed to facilitate penetration and engagement with the muscular wall of the heart.

The anchor member 302 can be formed from a single tube of shape memory material, such as, for example, Nitinol. During manufacture, the shape memory material may be cut using a mechanical or laser cutting tool. After cutting the tube, the expanded or flowered shape can be imparted to the memory of the shape memory material with techniques known in the art (e.g. heat setting the shape). Methods for manufacturing the anchor member are described in detail in Applicant's co-pending U.S. application Ser. No. 11/750, 272 (hereinafter "the '272 application"), which is incorporated herein by reference. In one preferred embodiment, the anchor member is formed to have an expanded configuration that conforms to the contours of the particular surface area of the heart where the anchor member is to be deployed, as described in the '272 application.

The surface of the anchor member 302, including the prongs 304, is desirably configured to promote tissue growth onto and even into its surface. In one example this growth is achieved by providing the anchor member with a relatively rough and/or porous surface. Additionally, biological coatings of the types known in the art can be included on the surface of the anchor member 302 to promote healing and tissue growth.

Figure 10:
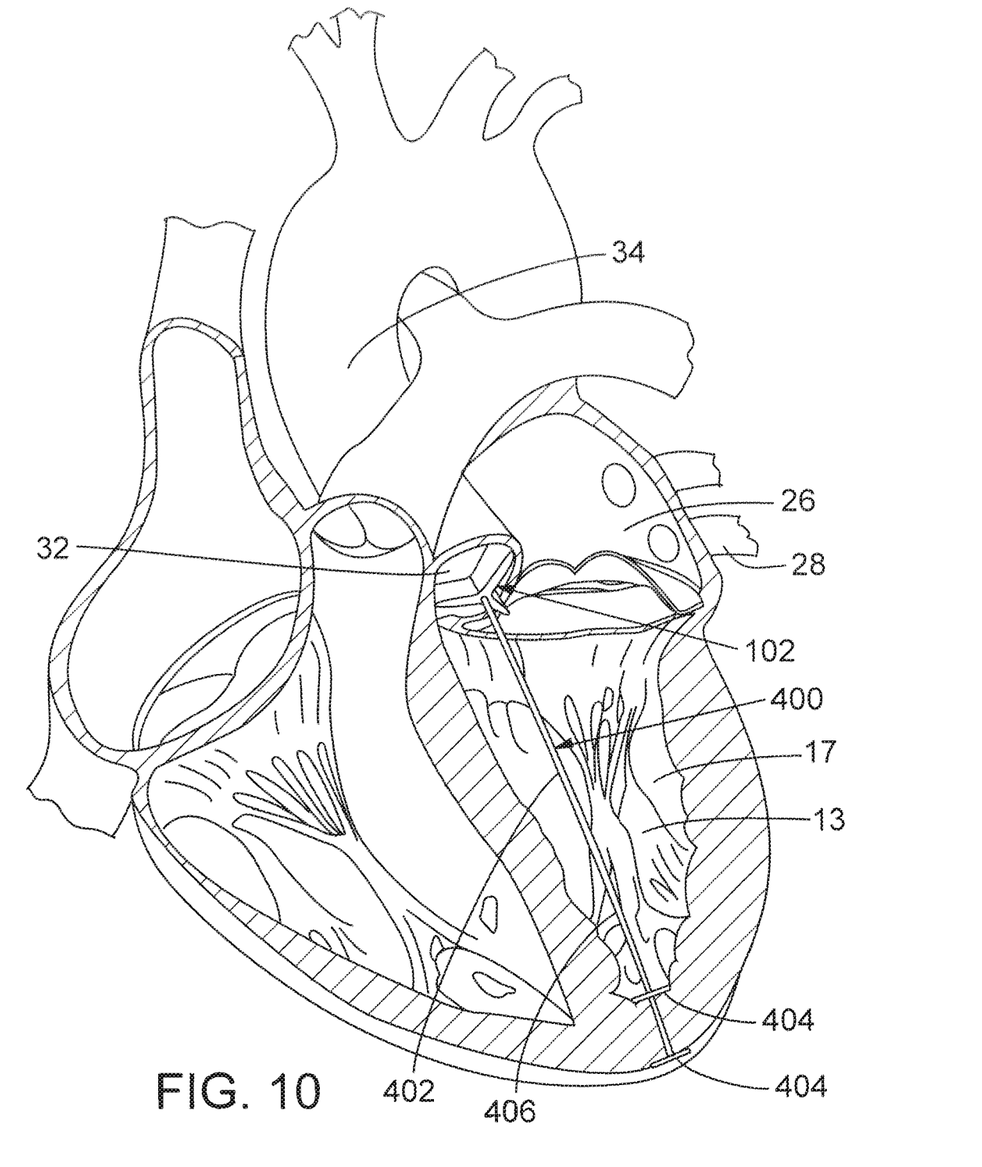
FIG. 10 is a variation of the embodiment shown in FIG. 9A wherein an alternative anchoring member is provided.

FIG. 10 illustrates another variation of an anchoring member 402 wherein one or more anchors, such as the illustrated plates 404, are located on opposite sides of the muscular wall of the heart for anchoring the prosthetic device 400 to the heart. The plates 404 can be formed of any biocompatible material, such as biocompatible metals or plastics. The anchoring member 402 includes a shaft 406 having an upper end portion connected to the insert member 102 and a lower-end portion that extends through the wall of the heart. One plate 404 is disposed on the shaft inside the left ventricle and another plate 404 is disposed on the shaft outside the left ventricle to secure the shaft in place.

If desired, the prosthetic device may be deployed in multiple stages wherein, in a first stage, the anchoring member is attached to the aorta (or ventricular wall) before the insert member is delivered. In a second stage, the insert member of the device is connected to the anchoring member at a later time (e.g., hours, days or weeks later). The time between the first and second stages advantageously allows tissue to heal and even grow over the anchoring member, thereby further embedding the anchoring member in the heart. Without the added stress that the insert member of the device may impart on the tissue, the healing and overgrowth may proceed more rapidly with less adverse affects (e.g., unwanted scarring). Additional details regarding exemplary anchoring members, expandable insert members and two-stage deployment can be found in the '272 application.

Figure 11:
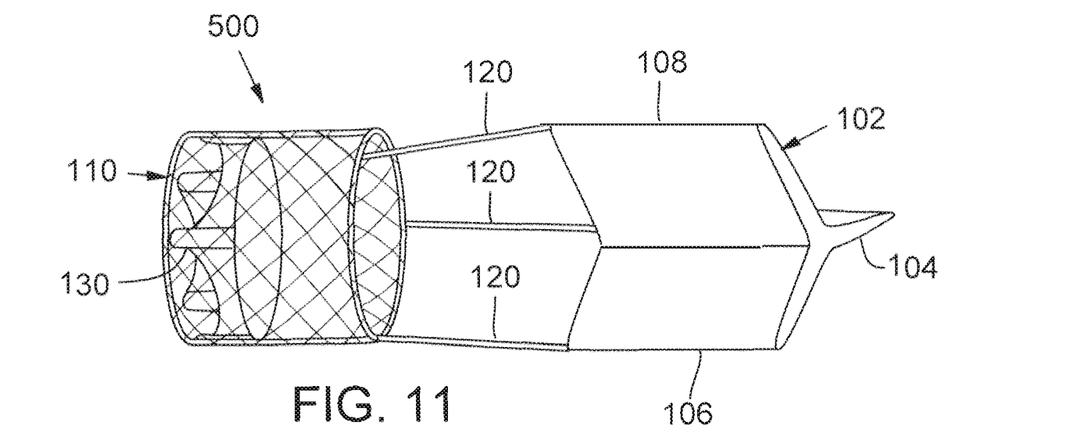
FIG. 11 is a perspective view of a prosthetic device similar to the embodiment illustrated in FIG. 2 wherein the anchoring member includes a stent and a valve member for deployment in the ascending aorta.

FIG. 11 shows another alternative embodiment of a prosthetic device, indicated at 500. The anchoring member 110 can be a stent and can include a valve member 130 mounted inside the stent. In the illustrated embodiment, the valve member 130 is a three-leaflet bioprosthetic valve. In particular examples, the anchoring member and valve member may take the form of the Cribier-Edwards valve manufactured by Edwards Lifesciences of Irvine, Calif. Additional details regarding exemplary embodiments of a stented valve can be found in U.S. Pat. No. 6,893,460, which is hereby incorporated by reference in its entirety.

The valve member 130 in the stent ensures unidirectional flow through the stent. The stent is desirably configured for delivery into an ascending aorta. The stent is expanded, either by self-expansion or by balloon expansion, such that the stent is anchored in the aorta. After deployment, the valve member in the stent prevents blood from flowing backward through the aorta. The insert member is delivered into the native aortic valve to improve the native valve function. Accordingly, two separate valves (i.e., the stented valve and the native valve) work in tandem for inhibiting regurgitation through the aortic annulus. By deploying the insert member in the native valve, the native valve is allowed to function as it should and blood is allowed to flow into the coronary arteries in a substantially natural manner. The stented valve supplements the function of the native valve. If desired, the stented valve could be constructed to close before or after the native valve to further influence and improve the native valve function and also to improve hemodynamics and/or perfusion into the coronary arteries.

Figure 12:
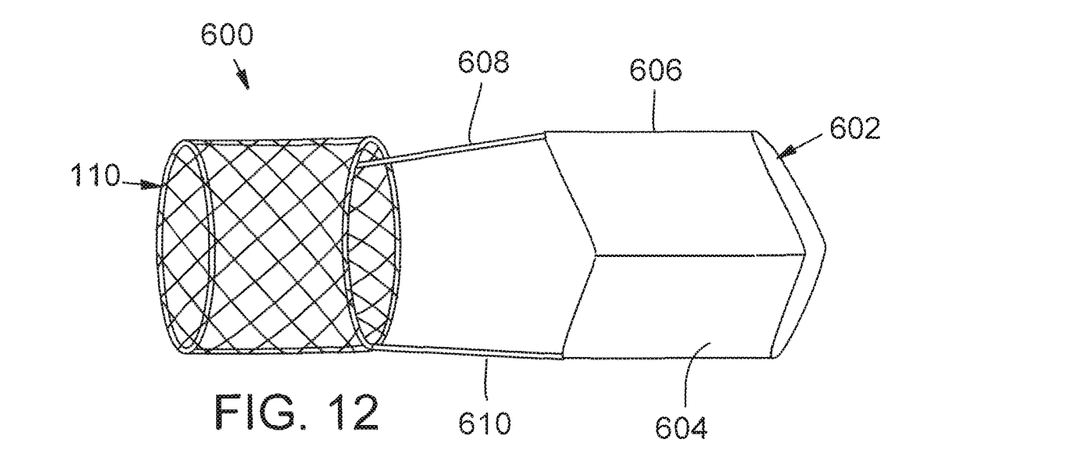
FIG. 12 is a perspective view of a prosthetic device similar to the embodiment illustrated in FIG. 2 in which the insert member is formed with two arms.

With reference to FIG. 12, a prosthetic device 600 according to yet another embodiment is provided. The prosthetic device 600 is configured for use in an abnormal aortic valve having only two leaflets. To treat this portion of the population, an insert member 602 is provided with two arms 604, 606 for filling the gaps between the leaflets. In addition, in certain aortic valves having three leaflets, it may not be necessary to fill gaps between each of the three leaflets. Accordingly, it may be desirable to use an insert member of the type shown in FIG. 12 for preventing or reducing regurgitation in a three leaflet valve.

For purposes of illustration, desirable embodiments of a prosthetic device have been described above for use in a valve normally having three leaflets, such as an aortic valve. However, it will be recognized by those of ordinary skill in the art that variations of the devices may also be used to treat another valve with three leaflets, such as a pulmonary valve, in an analogous manner. When used to treat the pulmonary valve, the anchoring member (e.g., stent) can be configured for deployment in the pulmonary trunk or a pulmonary artery. Alternatively, the anchoring member may be secured within the right ventricle.

Figure 13:
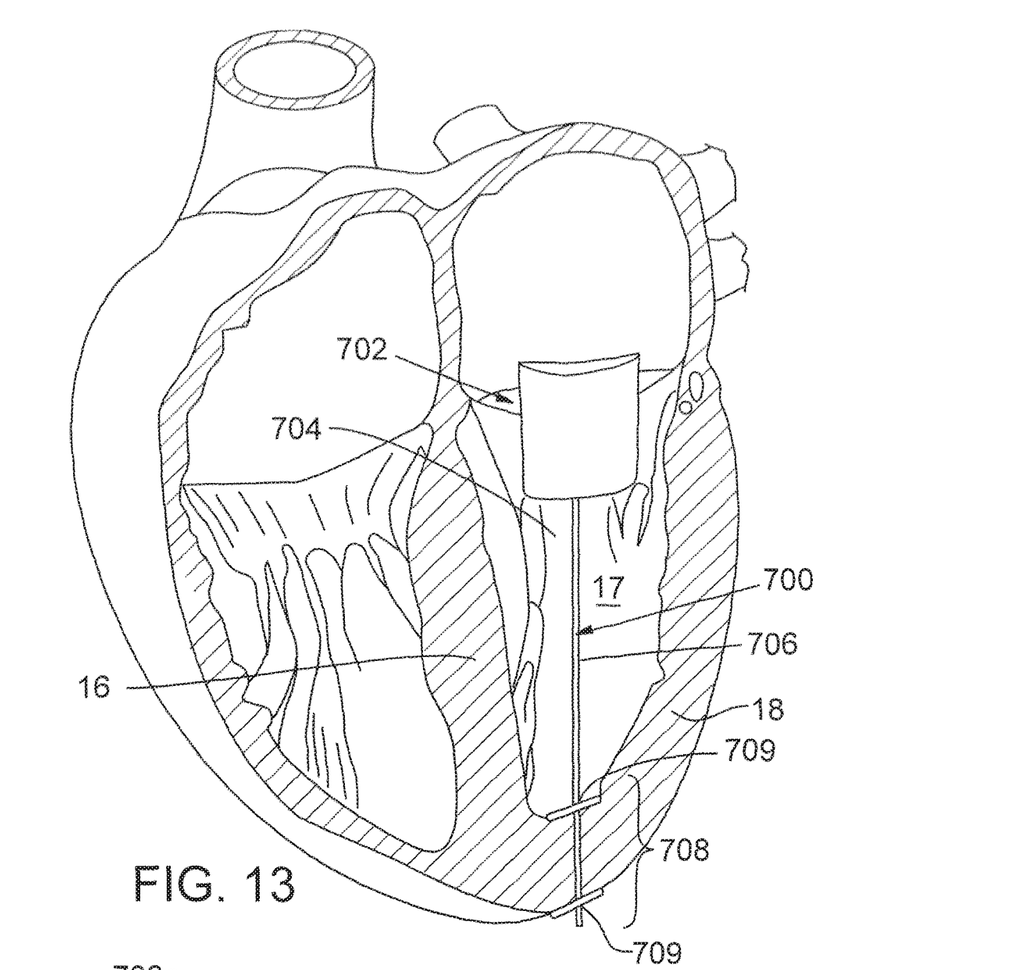
FIG. 13 is a perspective view of a prosthetic device including an anchoring member and an insert member deployed in a heart for treating an insufficient mitral valve.
Figures 14, 15:
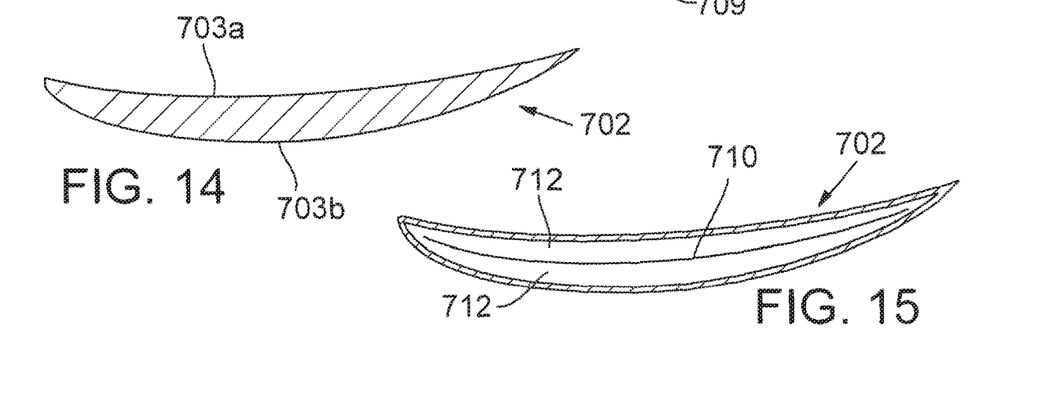
FIG. 14 is a cross-sectional view of the insert member of FIG. 13.
FIG. 15 is a cross-sectional view illustrating an insert member formed with a passageway and valve member for allowing blood to flow through the insert member in one direction.

With reference now to FIGS. 13 through 15, a prosthetic device 700 is configured for treating a bicuspid valve, such as a defective mitral valve. As illustrated in FIG. 13, the prosthetic device 700 includes an insert member 702 and an anchoring member 704. The insert member 702 comprises a body sized and shaped to fill the gap between the anterior and posterior leaflets of an insufficient mitral valve.

In one specific example, the insert member 102 exhibits sufficient rigidity to substantially maintain its deployed shape and is resilient and/or flexible enough to be compressed to a reduced diameter for delivery in a delivery sheath. The insert member can be formed from plastic, metal or other biocompatible material suitable for implantation into a subject. In particular examples, as described previously, the insert member can include an outer layer or sheath substantially formed of a biocompatible material, such as a cloth-like or fabric material (natural or synthetic) or a biological material, such as collagen or biological tissue material in order to protect the native leaflets from damage (e.g., to inhibit abrasion that could occur in response to engagement and disengagement of the leaflets). For instance, smooth animal pericardium such as equine, bovine, porcine or other animal pericardial tissue which is compatible with the native leaflets may be included within the outer layer. Such tissue may be tanned or fixed by a suitable tanning environment or the pericardium can be cross-linked with glutaraldehyde and heparin bonded by a detoxification process. In a certain example, the biological tissue material can be one of the NO-REACT® natural tissue products exhibit improved biocompatibility and mitigate calcification and thrombus formation. The outer layer can cover the entire outer surface of the insert member 102 or selected portions of the outer surface, such as those portions that come into contact with the native leaflets. The insert member 702 can be shaped with tapered and/or smooth edges to minimize or eliminate hemolytic effects.

The cross-sectional profile of the insert member 702 is shaped such that the native leaflets are capable of contacting the sides 703a and 703b of the insert member 702 to create a tight seal. As illustrated in FIGS. 13-15, the insert member 702 preferably has a crescent-shape cross-sectional profile to better conform to the curvature of the native leaflets. The surface of the insert member 702 can be of a compliancy that allows the native leaflets to engage the insert member 702 to create a tight seal without damaging the leaflets. For example, as described above, the surface can comprise a biocompatible material, such as collagen or pericardial tissue to inhibit abrasion that could occur in response to engagement or coaptation of the insert member surface with the native leaflets. In operation, the native leaflets of the mitral valve press against the walls of the insert member during ventricular systole to create a tight seal and prevent regurgitation of blood from the left ventricle into the left atrium.

In the illustrated embodiment, the anchoring member 704 of the prosthetic device 700 includes a shaft or elongated body portion 706, the lower end portion of which forms a penetration member 708. Plates 709 can be disposed on the penetration member 708 on opposite sides of the heart wall to secure the shaft in place. The body portion 706 and penetration member 708 of the anchoring member 704 may be of any suitable shape and material that imparts the material properties (elasticity, rigidity, resilience and the like) desired for each part of the device 700. For example, the penetration member 708 can be formed of any biocompatible material, such as biocompatible metals or plastics, which is capable of penetrating the left ventricle muscular wall to secure the insert member 702 to the heart without substantially impairing the wall.

In one example, the anchoring member 704 may be configured for deployment in the left ventricle. FIG. 14 is a cross-sectional view of the insert member 702 shown in FIG. 13. In this embodiment, the insert member 702 can have a substantially solid cross-section. In a variation, as shown in FIG. 15, the insert member 702 may include a passageway extending along a longitudinal axis. The passageway can be adapted to allow blood to flow through the insert member in one direction. A valve member can be included within the insert to ensure that blood flows in only one direction. In a particular example, the valve member can comprise one or more flap members 712 defining a slit or opening 710. The valve member mimics the function of the target valve by allowing blood flow in only one direction. Thus, blood flow passing into the passage from one direction opens the flaps and thereby passes through the insert member while blood moving into the passage from the opposite direction is stopped by the valve.

IV. System and Methods for Reducing Regurgitation Through a Heart Valve

Disclosed herein are a system and methods for treating a defective heart valve. In one embodiment, the system includes a prosthetic device including an anchoring member, such as a self-expandable anchoring member, and an insert member. The system can further include a delivery catheter for delivering the prosthetic device into the heart via a percutaneous approach. For example, the catheter can be introduced percutaneously into the patient's vasculature (e.g., into a peripheral artery such as the femoral artery) and advanced to the implantation site. In certain embodiments, for example, the catheter is sized for insertion through a small incision in the groin and has a length of at least about 80 cm, usually about 90-100 cm, to allow transluminal positioning of the shaft from the femoral and iliac arteries to the ascending aorta in a retrograde approach. Alternatively, the catheter may have a shorter length, e.g. about 20-60 cm, for introduction through other insertion points, such as, for example, the iliac artery, the brachial artery, the carotid or the subclavian arteries. In the femoral approach, the catheter desirably is long enough and flexible enough to traverse the path through the femoral artery, iliac artery, descending aorta and aortic arch. At the same time, the catheter desirably has sufficient pushability to be advanced to the ascending aorta by pushing on the proximal end, and has sufficient axial, bending, and torsional stiffness to allow the physician to control the position of the distal end, even when the catheter is in a tortuous vascular structure. Alternatively, the catheter may be passed through a port between ribs. In one technique, the catheter is advanced through the patient's thorax above the heart and through an incision in the aortic arch, in a so-called minimally-invasive procedure. In another technique, the catheter is advanced through an incision in the heart wall, preferably along the apex of the heart. The prosthetic device is advanced to the heart valve that is to be treated, and it is positioned to extend across the valve with the arms of the device interposed between the leaflets such that the leaflets of the valve close and press against the walls of the insert member to create a tight seal.

In certain embodiments, the delivery catheter includes an elongated sheath having a lumen sized to receive the prosthetic device. The prosthetic device is held within the sheath in a collapsed configuration during advancement through the subject's vasculature. For example, during advancement to the left ventricle, the device is initially contained within the delivery sheath with the anchoring member retained in a radially compressed state. In one variation, the distal portion of the delivery sheath is configured for retrograde advancement and may be configured with a deflectable end portion for facilitating navigation around the aortic arch. After reaching the treatment site, the sheath is moved proximally relative to the prosthetic device to eject the device from the sheath. The device is then allowed to expand such that the insert conforms to the gaps in the aortic valve and the anchoring member engages the inner wall of the aorta.

Although embodiments of the present invention are preferably configured for percutaneous or minimally-invasive delivery procedures, in certain situations, the insert member may be deployed via an open-heart surgical procedure. In these embodiments, a delivery catheter may not be necessary since the defective native valve can be directly accessed.

Although the disclosure has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the disclosure and should not be construed to limit the scope thereof.

What is claimed is:

1. A method of reducing regurgitation in a native heart valve having three native leaflets, the method comprising:
    inserting a delivery catheter through a small incision and into a patient's vasculature, the delivery catheter having a prosthetic device contained within a sheath along a distal end portion of the delivery catheter, the prosthetic device including a self-expanding insert member and an anchoring member, wherein at least one elongate connecting member couples the self-expanding insert member to the anchoring member, wherein the self-expanding insert member is shaped for deployment within a native heart valve having three native leaflets;
    advancing the distal end of the delivery catheter through a patient's vasculature and toward the heart valve;
    allowing the self-expanding insert member to self-expand in a gap between the native leaflets of the heart valve; and
    allowing the anchoring member to self-expand into engagement with an inner wall of a blood vessel, wherein the anchoring member takes the form of a stent having an open frame construction, the stent formed by a plurality of circumferential bands, each band including zig-zag struts shaped for engaging the inner wall of the blood vessel without penetrating tissue;
    wherein, after deployment of the prosthetic device, the native leaflets of the heart valve continue to function and form a tight seal against the self-expanding insert member for preventing regurgitation through the heart valve and wherein the stent secures the self-expanding insert member in a substantially fixed position within the heart valve and wherein the self-expanding insert member is spaced apart from the stent; and
    wherein the self-expanding insert member includes three arms that extend radially outwardly into gaps between the native leaflets, thereby reducing regurgitation when the native leaflets are in a closed position; and
    wherein the self-expanding insert member includes an internal passageway extending along a longitudinal axis, the passageway adapted for allowing blood to flow through the self-expanding insert member only when the native leaflets are in an open position.

2. The method of claim 1, wherein the insert member is shaped with tapered ends to minimize hemolytic effects.

3. The method of claim 1, wherein the insert member is covered with a biocompatible material and wherein the biocompatible material has a smooth surface for inhibiting abrasion along the native leaflets of the heart valve.

4. The method of claim 1, wherein the anchoring member is formed of a shape memory material.

5. The method of claim 1, wherein the sheath has a deflectable end portion for facilitating navigation.

6. The method of claim 5, wherein the prosthetic device is advanced relative to the sheath for allowing the insert member to self-expand.

7. The method of claim 6, wherein the insert member exhibits sufficient rigidity to substantially maintain a deployed shape within the heart valve after deployment and is flexible enough to be compressed to a reduced diameter for containment within the sheath.

8. A method of reducing regurgitation through a heart valve, the method comprising:
    inserting a delivery catheter into a patient's vasculature, the delivery catheter having a prosthetic device disposed along a distal end portion thereof, the prosthetic device including an insert member and an anchoring member, the insert member connected to the anchoring member by at least one elongate connecting member, the insert member shaped for filling a gap between three native leaflets of a heart valve for reducing regurgitation while allowing the three native leaflets to continue functioning, the anchoring member shaped for deployment within a blood vessel adjacent the heart valve for securing the insert member in a substantially fixed position;
    advancing the distal end portion of the delivery catheter through the patient's vasculature and toward the heart valve, wherein the prosthetic device is held within a sheath in a collapsed configuration during advancement through the patient's vasculature;
    retracting the sheath and allowing the insert member to self-expand between the native leaflets of the heart valve; and
    allowing the anchoring member to self-expand into engagement with the inner wall of the blood vessel, wherein the anchoring member takes the form of a self-expanding stent, the stent adapted to engage the inner wall of the blood vessel without penetrating tissue along the inner wall of the blood vessel;
    wherein, after deployment of the prosthetic device, the self-expanding insert member forms three radial arms that are positioned between the three native leaflets for reducing regurgitation through the heart valve when the three native leaflets are in a closed state; and
    wherein the self-expanding insert member includes an internal passageway extending along a longitudinal axis and wherein blood flows through the passageway only when the native leaflets are in an open state.

9. The method of claim 8, wherein the stent has an open-frame construction.

10. The method of claim 9, wherein the stent is made from a shape memory alloy.

11. The method of claim 10, wherein the stent includes circumferential bands, each band including a plurality of struts members arranged in a zig-zag configuration.

12. The method of claim 8, wherein the at least one connecting member provides a spacer such that the insert member is spaced apart from the anchoring member.

13. The method of claim 12, wherein the at least one connecting member is generally cylindrical in shape.

14. The method of claim 13, wherein the at least one connecting member has a length of about 6 mm to about 14 mm.

15. The method of claim 8, wherein the insert member comprises a shape memory material.

16. The method of claim 15, wherein the insert member further comprises a smooth biocompatible material cover for inhibiting abrasion.

17. The method of claim 16, wherein the biocompatible material is a fabric.

18. The method of claim 16, wherein the biocompatible material is pericardial tissue.

\* \* \* \* \*